United States Patent [19]

Yates

[11] 4,282,323

[45] Aug. 4, 1981

[54] REMOVAL AND CONCENTRATION OF LOWER MOLECULAR WEIGHT ORGANIC ACIDS FROM DILUTE SOLUTIONS

[75] Inventor: Richard A. Yates, Wilmington, Del.

[73] Assignee: E. I. Du Pont de Nemours and Company, Wilmington, Del.

[21] Appl. No.: 82,986

[22] Filed: Oct. 9, 1979

[51] Int. Cl.³ .......................... C12P 7/40; C12P 7/54; C12R 1/145

[52] U.S. Cl. .................................. 435/140; 435/136; 435/801; 435/842; 562/513

[58] Field of Search ............... 435/140, 141, 136, 801, 435/842; 562/513; 426/17

[56] References Cited

U.S. PATENT DOCUMENTS

| | | | |
|---|---|---|---|
| 2,697,724 | 12/1954 | Collier | 562/513 |
| 2,714,118 | 7/1955 | Copenhaver et al. | 562/513 |
| 2,744,927 | 5/1956 | Copenhaver et al. | 562/513 |
| 2,913,310 | 11/1959 | Sandborn et al. | 562/513 |
| 2,974,081 | 3/1961 | Biggs et al. | 162/33 |
| 3,734,773 | 5/1973 | Haley | 562/513 |
| 3,997,599 | 12/1976 | Grinstead | 562/513 |

FOREIGN PATENT DOCUMENTS 572664 10/1945 United Kingdom ..................... 435/140

OTHER PUBLICATIONS

Buchanan, R. E. & Gibbons, N. E. Eds., *Bergey's Manual of Determinative Bacteriology*, Eighth Edition; 1974; p. 551.

*Primary Examiner*—Alvin E. Tanenholtz
*Assistant Examiner*—Elizabeth J. Curtin

[57] ABSTRACT

A process for obtaining lower carboxylic acids from aqueous lower carboxylic acid salts, such as obtained from a fermenter. The process involves converting the lower carboxylic acid salt to the corresponding acid with carbon dioxide, extracting the thus formed acid with a solvent and using the thus formed bicarbonate salt to buffer the fermenter.

21 Claims, 2 Drawing Figures

4,282,323

REMOVAL AND CONCENTRATION OF LOWER MOLECULAR WEIGHT ORGANIC ACIDS FROM DILUTE SOLUTIONS

BACKGROUND OF THE INVENTION

Field of the Invention

The present invention relates to a process for recovering organic acids, such as acetic acid or butyric acid, from aqueous source solutions such as fermentation broths.

At the present time there are two basic synthetic methods for the preparation of acetic acid for industrial use. The first comprises the oxidation of natural gas to methanol followed by reaction of methanol with carbon monoxide over a noble metal catalyst to form acetic acid. The second, and older method of production of acetic acid, comprises oxidizing ethylene oxide to acetic acid. Both of these processes are based on natural gas and the cost is expected to increase markedly in the next few years.

All consumable acetic acid is prepared by the vinegar process which comprises the two steps of (1) fermenting glucose in the presence of microorganisms to produce ethanol and (2) oxidizing ethanol to acetic acid. One mole of glucose produces two moles of acetic acid. At present this process is far too expensive for industrial acetic acid production.

More recently, organisms such as *Clostridium thermoaceticum* have been discovered that can convert carbohydrate to acetic acid in yields of 80% or greater (100% in theory). Many organisms, which are attractive from a fermentation yield basis, cannot tolerate highly acid conditions. Hence, the organic acids must be partly neutralized as they are formed. This creates the problem of isolating a pure acid from an aqueous solution where it occurs primarily as the acid salt. In other cases as well, such as chemical process streams or waste streams, it is necessary to recover pure acids from aqueous solutions where the acid occurs primarily as the salt.

The approach used in the past has been to add a strong mineral acid, such as sulfuric acid, to the organic salt solution, and extract the resulting organic acid into an organic solvent for eventual recovery by distillation. This "consumables" approach necessitates adding an alkali to the fermentation liquor (or other solution) to maintain neutrality during culture (or other processing), adding sulfuric acid to the "waste liquor" to permit organic acid extraction, and then disposing of the resulting waste salt. In the case of theoretical glucose fermentation to acetic acid, the overall materials are:

2 glucose→6 acetic acid+6NaOH→6NaAc+6H$_2$O, 3H$_2$SO$_4$+6NaAc→6HAc+3Na$_2$SO$_4$. By weight: 360 g glucose+240 g NaOH+294 g H$_2$SO$_4$→360 g HAc+426 g Na$_2$SO$_4$+108 g H$_2$O.

The present process permits recovery of acids, such as acetic acid, from fermentation liquors without the use of any consumable salts or acids or the disposal problem for the resulting by-product salt. In the present process as applied to fermentation, all materials with the exception of the fermentation substrates are recoverable and recyclable.

SUMMARY OF THE INVENTION

In the present invention, as applied to fermentation, a fermentation substrate of carbohydrate, which preferably is a sugar such as glucose or xylose, is fermented in the presence of a bacterial microorganism such as *Clostridium thermoaceticum* and in the presence of an alkali metal bicarbonate, such as sodium bicarbonate, to form a salt of the acid (e.g., sodium acetate) plus carbon dioxide. The presence of the bicarbonate is advantageous since it can be used to buffer the fermenter wherever an organism cannot tolerate low pH. Alkaline earth salts can be used as well as alkali metal salts, provided that the organisms can tolerate the salt used. Generally this process applies when it is desirable to maintain the fermenter at pH 5 to 8.

The fermentation liquor may be extracted directly by solvent plus carbon dioxide under pressure or be passed through a solids extractor countercurrent to an ion exchange resin charged with bicarbonate, to selectively extract acetate out of the liquor and return alkali metal bicarbonate to the fermenter. The preferred solvents form azeotropes with water. When an ion exchange resin is used, the organic acid form of the ion exchange resin can be extracted directly, countercurrently, by closing and opening appropriate valves, or be passed through a countercurrent solids extractor charged with carbon dioxide under pressure in the presence of a water-containing organic solvent, such as, but not limited to, t-butanol, 2-butanone, dimethyl ether or diethyl ether, to convert bound salt to free acid. Advantage can be taken of changes in relative affinity of resin for ions with change of temperature. The bicarbonate resulting from the CO$_2$ generated carbonic acid is bound to the resin, and the resin thus reactivated in bicarbonate form is reused with the fermentation liquor. The free organic acid in the solvent is purified from the solvent by conventional means such as distillation or recrystallization. Solvent and water are returned to the system. Carbon dioxide is also recycled through the system, but a slight excess may be generated by fermentation connected with cell growth.

DETAILED DESCRIPTION OF THE DRAWINGS

Figure 1:
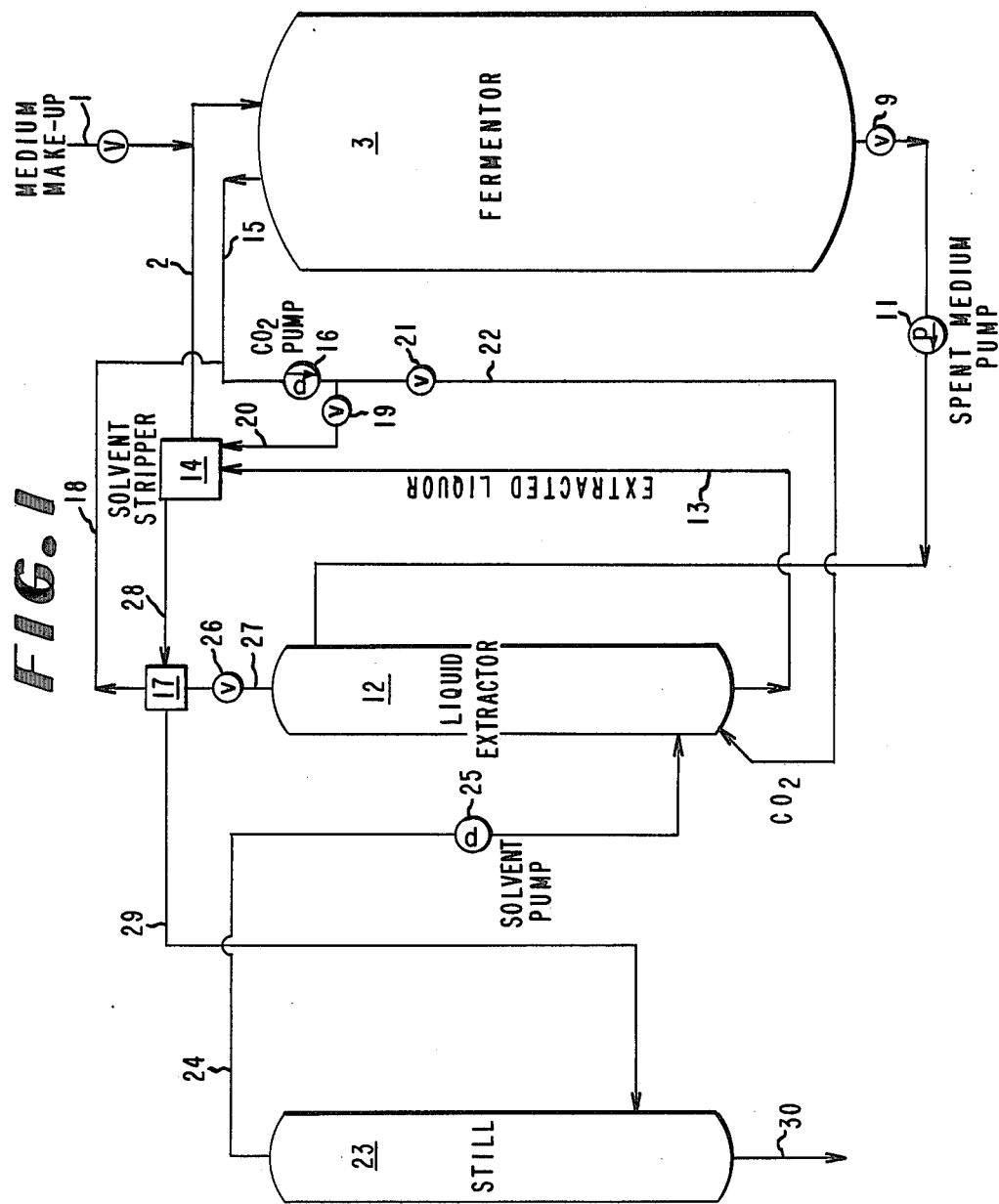
FIG. 1 is a flow sheet of the process of the present invention using direct extraction of acid from a fermenter using solvent and carbon dioxide.

Referring now to FIG. 1, a suitable nutrient solution containing carbohydrate is fed by means of line 1 into recycle line 2 and then into fermenter 3. As an example of operation within fermenter 3, glucose is converted into acetic acid by the action of microorganisms. The acetic acid is reacted with sodium bicarbonate to form sodium acetate plus carbon dioxide and maintains the pH of the fermenter somewhat above the pKa of acetic acid. Cell free medium can be removed directly from fermenter 3 by use of cell hold-back via line 9. The medium is pumped into extractor 12 via pump 11. Extracted spent medium is removed from extractor 12 by line 13 into solvent stripper 14 and returned to fermenter 3 by line 2. Solvent and gas are transported from stripper 14 to gas stripper 17 by line 28. Carbon dioxide produced by fermentation of glucose and neutralization of sodium bicarbonate in fermenter 3 is collected and transported by line 15 to pump 16, and combined with carbon dioxide from gas stripper 17 transported by line 18. Pump 16 pressurizes the carbon dioxide and feeds part of the carbon dioxide into solvent stripper 14 through valve 19 and line 20, and the remainder of the carbon dioxide through valve 21 and line 22 into extractor 12. Solvent plus entrained water is fed into extractor 12 from distillation column 23 via line 24 and pump 25. Solvent, acetic acid, carbon dioxide and water are removed from extractor 12 through valve 26 and line 27 into gas stripper 17 where carbon dioxide is removed, then transported to distillation column 23 by line 29. Solvent and water are removed by distillation and returned to the system by line 24 as described above, and acetic acid is removed by line 30. The headspace of extractor 12 is designed as a solvent stripper to prevent entrainment of medium with the solvent into the distillation column. Alternately the solvent stream from extractor 12 can be fed to a solvent stripper before gas stripper 17 to serve the same purpose (not shown).

Figure 2:
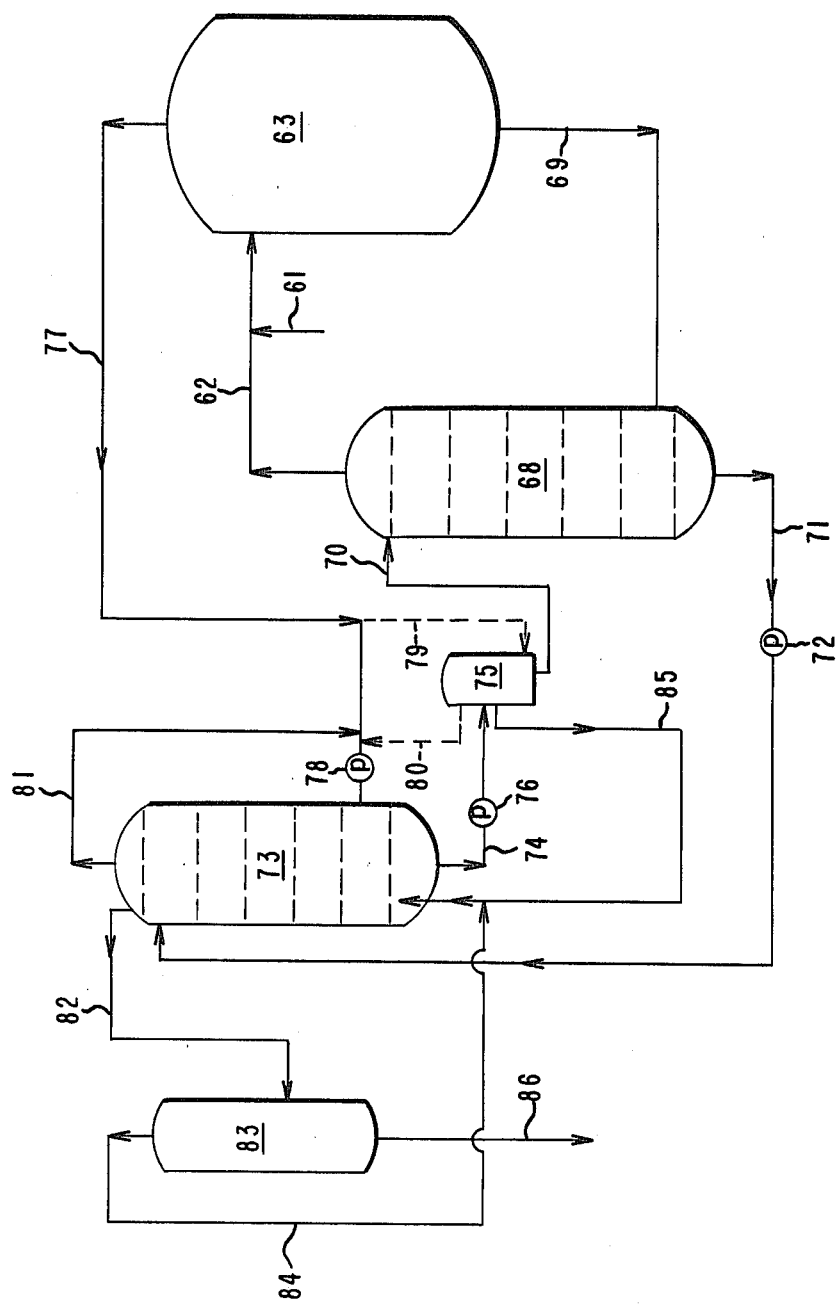
FIG. 2 is a flow sheet of the process of the present invention using countercurrent ion exchange extraction of acid from a fermenter.

Referring now to FIG. 2, an alternate extraction system using countercurrent ion exchangers is described. A suitable nutrient solution containing carbohydrate is fed by means of line 61 into recycle line 62 and then into fermenter 63. As an example of operation within fermenter 63 glucose is converted into acetic acid by the action of microorganisms. The acetic acid is reacted with sodium bicarbonate to form sodium acetate and maintain the pH of the fermenter medium somewhat above the pKa of acetic acid. Spent medium liquid can be taken off from fermenter 63 by means of cell hold-back via line 69 to form the sodium acetate feed to ion exchanger 68. Anion exchange resin in the bicarbonate form is fed to countercurrent ion exchanger 68 by means of line 70. Anion exchange resin in the acetate form is removed from countercurrent ion exchanger 68 by means of line 71 and pumped by pump 72 to countercurrent ion exchanger 73. Sodium bicarbonate is removed from countercurrent ion exchanger 68 by means of line 62 and fed to fermenter 63. Anion exchange resin in the bicarbonate form is removed from countercurrent ion exchanger 73 by means of line 74 and pumped to solvent stripper 75 by pump 76. Carbon dioxide is removed from fermenter 63 by means of line 77 and pumped to countercurrent ion exchanger 73 by means of pump 78. Alternatively part or all of the carbon dioxide in line 77 may be fed to solvent stripper 75 by means of line 79. Carbon dioxide and entrained solvent from solvent stripper 75 can be removed from solvent stripper 75 by means of line 80 and fed to countercurrent ion exchanger 73. Carbon dioxide is removed from the top of countercurrent ion exchanger 73 by means of line 81, combined with the carbon dioxide in line 77 and returned to countercurrent ion exchanger 73. Acetic acid and the azeotrope of solvent and water are removed from countercurrent ion exchanger 73 by means of line 82 and fed to distillation column 83. The solvent-water azeotrope is removed from distillation column 83 by means of line 84 and returned to countercurrent ion exchanger 73 along with solvent in line 85 being returned from solvent stripper 75. Crude dry acetic acid is recovered from distillation column in line 86.

DETAILED DESCRIPTION

The dilute aqueous solution of organic salts suitable for use in the present invention can be obtained from several sources such as fermenter and process streams. Further by controlling conditions, salts of different organic acids can be separated from each other using the process of the present invention.

Preferred salts of organic acids include salts of aliphatic monocarboxylic acids containing from 1 to 20 carbon atoms such as formic acid, acetic acid, butyric acid, caproic acid, lauric acid, and stearic acid. Other preferred salts of organic acids include salts of olefinic monocarboxylic acids containing from 3 to 20 carbon atoms such as acrylic acid, methacrylic acid, ethacrylic acid and oleic acid. Other preferred salts include salts of aromatic carboxylic acids containing from 7 to 20 carbon atoms such as benzoic acid. Other less preferred salts of organic acids include salts of aliphatic dicarboxylic acids containing from 2 to 20 carbon atoms such as oxalic acid, adipic acid and dodecanedioic acid. Other less preferred salts include salts of olefinic dicarboxylic acids containing from 4 to 20 carbon atoms such as fumaric acid, maleic acid, itaconic acid and dimethylmuconic acid. Other less preferred salts include salts of aromatic dicarboxylic acids containing from 8 to 20 carbon atoms such as isophthalic acid and terephthalic acid. These acids may contain various substituents such as hydroxyl groups. Such salts include salts of p-hydroxybenzoic acid.

Generally the solvent used will be a polar organic solvent boiling at from $-30°$ to $90°$ C. Preferably the polar group or groups will be a hydroxyl group, keto group or aldo group. When the source of the carboxylic acid salt is a fermenter the solvent should not be toxic to the cells in the residual concentration dissolved in the aqueous phase and the solvent concentrations should not build up in the fermenter upon continuous recycle. When using *Clostridium thermoaceticum*, t-butanol at 0.7% and 2-butanone at 0.3% depress cell growth rates to about 25% of the control cell growth rate but at one-tenth of these concentrations cell growth rate is about 80% of the control growth rate. Build-up of low boiling solvent can be prevented by slow stripping of the fermenter with a stream of carbon dioxide.

Generally the solvent extraction will be carried out at from $0°$ to $80°$ C. using a volume solvent to volume water ratio of 0.1 to 1 to 10 to 1.

When using the ion exchange resin the temperature generally will be from $0°$ to $75°$ C. Advantageously the temperature to remove the acid from the ion exchange resin is at least $10°$ C. higher or lower than the temperature used to load the acid on the ion exchange resin depending on the resin being used.

The extraction can be carried out under pressure. Suitable partial pressures for carbon dioxide range from 1 to 1100 psig ($6.9 \times 10^3$ to $7584 \times 10^3$ pascals gauge Pag) and preferably 10 to 750 psig ($68.9 \times 10^3$ to $5171 \times 10^3$ Pag).

A typical operation of fermentation to produce the acid salts used in the extraction process of the present invention is as follows:

Flasks (erlenmeyer, 250 ml) were sterilized and charged with 150 ml sterile medium of the following composition:

| Component | mN | g/l |
| --- | --- | --- |
| Glucose | 100 | 18 |
| KH$_2$PO$_4$ | 40 | 5.5 |
| K$_2$HPO$_4$ | 40 | 7.0 |
| NaHCO$_3$ | 200 | 16.8 |
| MgSO$_4$ . 7H$_2$O | 1 | 0.25 |
| (NH$_4$)$_2$SO$_4$ | 7.6 | 1.0 |
| HSCH$_2$CO$_2$Na | 4.4 | 0.5 |
| Na$_2$MoO$_4$ . 2H$_2$O | .01 | .0024 |
| FeSO$_4$ . 7H$_2$O | .018 | .0050 |

-continued

| Component | mN | g/l |
|---|---|---|
| (NH$_4$Z)$_2$HC$_6$H$_5$O$_7$ | .018 | .0040 |
| Co(NO$_3$)$_2$ · 6H$_2$O | .01 | .003 |
| Na$_2$SeO$_3$ | .001 | .0002 |
| Na$_2$WO$_4$ · 2H$_2$O | .01 | .0033 |
| Yeast extract | | 5. |
| Tryptone | | 5. |
| NaCl | | 400. |

Flasks were bubbled with carbon dioxide and conditioned to 59° C., then inoculated with a vegetative culture of *Clostridium thermoaceticum* adapted to the medium used. Cultures were continued until glucose was exhausted, then aliquots were centrifuged to remove cells and the spent culture media treated as described in Example 1.

EXAMPLE 1

Extraction of acetic acid from acetate: Fermentation broth aliquots of 5.0 ml spent fermentation culture (pH about 6), centrifuged to remove cells, were obtained and transferred to stoppered, screw capped 15 ml glass tubes. To each tube was added an equal volume (5.0 ml) of water saturated 2-butanone (methyl ethyl ketone). The tubes were sealed, evacuated, and CO$_2$ was added with shaking at room temperature until the internal pressure was about 2 atmospheres (2.026×10$^5$ Pag). Control tubes without CO$_2$ added were also prepared. Aliquots of the organic phase were diluted into 20 volumes of water and assayed for acetic acid by gas chromatography. Acidification of these diluted extracts with hydrochloric acid gave no appreciable increase in detectable acetic acid. The total acetate content of the original fermentation cultures was assayed by gas chromatography of acidified samples, and the ratio of acetic acid in organic phase with CO$_2$ treatment (minus control sample) to total fermentate acetate was determined. The amount of acetic acid extracted by 2-butanone plus CO$_2$ was 4.8% of the total acetate present.

EXAMPLE 2

Alterations of relative resin binding constant for acetate/bicarbonate with temperature were determined using aliquots of IRA-68, a weakly basic anion exchange resin possessing tertiary amine functionality in a cross-linked acrylic matrix. Blotted wet samples of resin preloaded with acetate or bicarbonate were equilibrated with solutions of the other salt at 30° and at 60° as follows: 1.5 ml of 1.0 N NaHCO$_3$+1.5 g IRA-68-acetate @ 1.2 meqv/g, and 1.0 ml 2 N sodium acetate+1.5 g IRA-68-bicarbonate. The residual solution plus 3 water washes (equilibrated at the original temperature) were collected, volumes measured, and assayed for acetate, and the total free acetate determined. The washed resin samples were treated with 5 successive extractions with hydrochloric acid and the total acetate released was measured. Equilibrium constants were determined by the relation $$K = \frac{\text{(acetate in solution) (bicarbonate on resin)}}{\text{(acetate on resin) (bicarbonate in solution)}},$$

and the average constant at 60° divided by the constant at 30°. The resultant ratio of 1.9 indicates that, relatively, acetate preferentially loads onto the resin with fermentate (containing sodium acetate) at 30°, and contacting with organic solvent plus CO$_2$ at 60° should remove more acetic acid into the organic extract than would the opposite temperature treatment.

| Condition | | | Total μ Moles Recovered | | K Observed |
|---|---|---|---|---|---|
| 1.8 meqv Resin | Solution | Temp. | Original Supt. Plus H$_2$O Washes | All HCl Extracts | |
| A HCO$_3$$^-$ | Ac$^-$ (2 meqv) | 60° | 1426 | 518 | 6.9 |
| B Ac$^-$ | HCO$_3$$^-$ (1.5 meqv) | 60° | 1270 | 508 | 13.8 |
| C HCO$_3$$^-$ | Ac | 30° | 1388 | 613 | 4.4 |
| D Ac$^-$ | HCO$_3$ | 30° | 1182 | 656 | 6.7 |

EXAMPLE 3

Fifteen ml of a 0.5 M sodium acetate in a solution of 24 wt % 2 butanone and 76 wt % water (lower phase) were mixed with 15 ml of a mixture of 88 wt % 2-butanone and 12 wt % water (upper phase) in a 75 ml shaker bomb. The bomb was shaken for 20 minutes while being maintained at 28°±2° C. and 750±100 psig (5171±689 Pag) of carbon dioxide. The bomb was held still for an additional 20 minutes while the phases separated, after which the pressure was slowly released. The top several ml of the top phase were removed and analyzed for acetic acid. About 0.08 molal acetic acid was found (16% of initial acetate).

EXAMPLE 4

Example 3 is repeated except 0.25 molal calcium acetate was charged to the shaker in the lower phase and 0.06 molal acetic acid was recovered in the upper phase.

EXAMPLE 5

Extraction of acetic acid from calcium acetate by t-butanol plus CO$_2$: A 2.0 ml aliquot of 1.06 M calcium acetate was extracted with 2.0 ml t-butanol at room temperature and pressure combined with slow bubbling of carbon dioxide gas for 5 minutes. The resultant organic phase contained 0.39 M acetic acid, or 18% of the acetate initially present.

EXAMPLE 6

IRA-68 resin aliquots preloaded with acetate, butyrate, and caproate were extracted with 2-butanone plus CO$_2$ gas at 1 atmosphere pressure (1.013×10$^5$ Pag) and room temperature. In each case 2.0 g wet resin containing 1.7 meqv acetic and butyric acid per gram wet resin and 1.0 meqv caproic per gram were washed with 2.0 ml water-saturated 2-butanone then extracted with 2.0 ml water-saturated 2-butanone plus carbon dioxide gas at 1 atmosphere pressure (1.013×10$^5$ Pag) by shaking for 3 minutes. Aliquots of the upper (2-butanone rich) phase and lower (water rich) phases were assayed for organic acid by dilution and gas chromatography. Results are shown below:

| Acid | Upper Phase mM | % Acid Removed @ 1 Volume 2-Butanone/Resin | Acid Partition Top Phase/Bottom Phase (Resin) |
|---|---|---|---|
| Acetic | 30 | 2 | 1.2 |
| Butyric | 126 | 7 | 5.8 |

-continued

| Acid | Upper Phase mM | % Acid Removed @ 1 Volume 2-Butanone/Resin | Acid Partition Top Phase/Bottom Phase (Resin) |
|---|---|---|---|
| Caproic | 250 | 29 | 11.4 |

I claim:

1. A process of recovering a carboxylic acid containing from 1 to 20 carbon atoms from an aqueous source solution of an alkali metal, alkaline earth metal or ammonium salt of said carboxylic acid comprising contacting said aqueous solution, in the presence of a liquid polar organic solvent having a boiling point of from −30° to 90° C., with carbon dioxide under pressure, to convert at least part of said salt to the corresponding acid, whereby said acid is dissolved in said solvent, and recovering said acid therefrom.

2. The process of claim 1 wherein said source solution is pressured with carbon dioxide to form the bicarbonate ion and the carboxylic acid.

3. The process of claim 2 wherein the source solution is the effluent from a fermenter.

4. The process of claim 3 wherein the bicarbonate salt formed by pressuring with carbon dioxide and extracting the fermenter effluent is recycled to the fermenter to buffer the pH of the fermenter.

5. The process of claim 4 wherein the water, polar organic solvent, and the carboxylic acid are distilled to separate crude carboxylic acid and an azeotrope of the polar organic solvent and water which azeotrope is recycled to extract the carboxylic acid from the fermenter effluent.

6. The process of claim 5 wherein the fermenter is operated under anaerobic conditions and carbon dioxide obtained from the fermenter is used to pressurize the fermenter effluent.

7. The process of claim 6 wherein the fermenter is maintained at a pH of between 5 and 8.

8. The process of claim 7 wherein the carboxylic acid salt produced in the fermenter is a salt of acetic acid.

9. The process of claim 8 wherein the salt is sodium acetate.

10. A process of recovering a carboxylic acid containing from 1 to 20 carbon atoms from an aqueous source solution of an alkali metal, alkaline earth metal or ammonium salt of said carboxylic acid comprising the steps of:

(1) contacting the bicarbonate form of an anion exchange resin with said aqueous source solution to give the carboxylate form of said resin and an aqueous bicarbonate solution, (2) separating the products of step (1), (3) in a second ion exchange step, contacting the carboxylate form of said resin with carbon dioxide under pressure and a mixture of a polar organic solvent having a boiling point of from −30° to 90° C. and water to free the carboxylic acid and to produce the bicarbonate form of said resin, (4) separating the product of step (3), and (5) recycling the bicarbonate form of said resin to step (1).

11. The process of claim 10 wherein the water, polar organic solvent and the carboxylic acid which are separated from the second ion exchange step are distilled to separate crude carboxylic acid from an azeotrope of water and the polar organic solvent.

12. The process of claim 11 wherein the bicarbonate form of the anion exchange resin being returned from the second ion exchange step is fed to a solvent stripper prior to being returned to the first ion exchange step.

13. The process of claim 12 wherein the temperature used to form the carboxylate form of the ion exchange resin is at least 10° C. different than the temperature used to form the bicarbonate form of the ion exchange resin.

14. The process of claim 13 wherein the carboxylic acid salt being fed to the first ion exchanger is a dilute solution obtained from a fermenter.

15. The process of claim 14 wherein the fermenter is operated under anaerobic conditions and carbon dioxide obtained from the fermenter is fed to the second ion exchange step to convert the carboxylate form of the anion exchange resin to the bicarbonate form of the ion exchange resin.

16. The process of claim 15 wherein the bicarbonate generated in the first ion exchange step is fed to the fermenter to neutralize the carboxylic acid generated in the fermenter.

17. The process of claim 16 wherein the fermenter is maintained at a pH between 5 and 8.

18. The process of claim 17 wherein the carboxylic acid salt produced in the fermenter is a salt of acetic acid.

19. The process of claim 18 wherein the salt is sodium acetate.

20. The process of claim 19 wherein both ion exchange steps are performed with countercurrent ion exchangers.

21. The process of claim 20 wherein the microorganisms in the fermenter consist essentially of *Clostridium thermoaceticum*.

* * * * *